(12) United States Patent
Turner et al.

(10) Patent No.: US 8,306,628 B2
(45) Date of Patent: Nov. 6, 2012

(54) DEEP HEATING HYPERTHERMIA USING PHASED ARRAYS AND PATIENT POSITIONING

(75) Inventors: Paul F. Turner, Bountiful, UT (US); Mark Hagmann, West Valley, UT (US); Thomas L. Youd, Salt Lake City, UT (US)

(73) Assignee: BDS Medical Corporation, West Valley, UT (US)

( * ) Notice: Subject to any disclaimer, the term of this patent is extended or adjusted under 35 U.S.C. 154(b) by 337 days.

(21) Appl. No.: 12/755,185

(22) Filed: Apr. 6, 2010

(65) Prior Publication Data
US 2011/0245900 A1 Oct. 6, 2011

(51) Int. Cl.
*A61F 2/00* (2006.01)
(52) U.S. Cl. .................... 607/101; 607/100; 607/102
(58) Field of Classification Search .......... 607/100–102, 607/156
See application file for complete search history.

(56) References Cited

U.S. PATENT DOCUMENTS

| | | | |
|---|---|---|---|
| 3,806,109 A * | 4/1974 | Weber et al. ............... 5/610 |
| 4,271,848 A | 6/1981 | Turner et al. |
| 4,403,618 A | 9/1983 | Turner |
| 4,462,412 A | 7/1984 | Turner |
| 4,586,516 A | 5/1986 | Turner |
| 4,589,423 A * | 5/1986 | Turner ................... 607/154 |
| 4,618,133 A | 10/1986 | Siczek |
| 4,638,813 A | 1/1987 | Turner |
| 4,669,475 A | 6/1987 | Turner |
| 4,672,980 A | 6/1987 | Turner |
| 4,697,802 A | 10/1987 | Brendl et al. |
| 4,712,559 A | 12/1987 | Turner |
| 4,798,215 A | 1/1989 | Turner |
| 4,860,752 A | 8/1989 | Turner |
| 4,974,587 A | 12/1990 | Turner et al. |
| 5,097,844 A | 3/1992 | Turner |
| 5,361,436 A | 11/1994 | Hahn |
| 5,446,548 A | 8/1995 | Gerig et al. |
| 5,790,996 A | 8/1998 | Narfstrom |
| 5,825,843 A | 10/1998 | Kobayashi |
| 5,919,135 A * | 7/1999 | Lemelson ............... 600/407 |
| 5,983,424 A | 11/1999 | Naslund |
| 6,138,302 A | 10/2000 | Sashin et al. |

(Continued)

OTHER PUBLICATIONS

1990 International Symposium Digest Antennas and Propagation vol. I, Institute of Electrical and Electronics Engineers, IEEE Catalog No. 90 CH2776-3, Library of Congress No. 89-80729, Dallas, TX, May 7-11, 1990, 1 page.

(Continued)

*Primary Examiner* — Roy Gibson
(74) *Attorney, Agent, or Firm* — Thorpe North & Western LLP

(57) ABSTRACT

A hyperthermia treatment system for heating a selected region within a target body that includes a power source and a plurality of electromagnetic applicators that are in electrical communication with the power source and arranged in a surrounding array around a focal region to concentrate their combined radiation output onto the focal region. The treatment system also includes a support mechanism that is adapted to support a target body within the surrounding array of applicators, and a positioning mechanism adapted to move the support mechanism and align the selected region within the target body with the focal region. Furthermore, the positioning mechanism is adapted to compensate for movement of the focal region in response to an interaction between the combined radiation output and the target body.

22 Claims, 9 Drawing Sheets

U.S. PATENT DOCUMENTS

| | | | |
|---|---|---|---|
| 6,246,239 | B1 | 6/2001 | Krogmann et al. |
| 6,279,579 | B1 | 8/2001 | Riaziat et al. |
| 6,414,490 | B1 | 7/2002 | Damadian et al. |
| 6,662,036 | B2 | 12/2003 | Cosman |
| 6,832,400 | B2 * | 12/2004 | Loveday et al. ............... 5/601 |
| 6,865,253 | B2 | 3/2005 | Blumhofer et al. |
| 7,093,311 | B2 | 8/2006 | Gnoyke |
| 7,154,991 | B2 | 12/2006 | Earnst et al. |
| 7,199,382 | B2 * | 4/2007 | Rigney et al. ............ 250/492.1 |
| 7,375,521 | B1 | 5/2008 | Damadian et al. |
| 7,565,207 | B2 | 7/2009 | Turner et al. |
| 7,643,661 | B2 | 1/2010 | Ruchala et al. |
| 2003/0164459 | A1 | 9/2003 | Schardt et al. |
| 2004/0028188 | A1 | 2/2004 | Amann et al. |
| 2004/0184583 | A1 | 9/2004 | Nagamine et al. |
| 2006/0002511 | A1 | 1/2006 | Miller et al. |
| 2008/0228063 | A1 | 9/2008 | Turner |
| 2008/0234865 | A1 | 9/2008 | Sommer |

OTHER PUBLICATIONS

S. Uehara, J. Omagari, K. Hata, "Modification of annular phased array heating pattern", Strahlemther. Onkol, 1989, p. 742, vol. 165, No. 10.

A. J. Fenn, et.al, "Focused Near-Field Adaptive Nulling: Experimental Investigation", 1990, 2 pages.

Giorgio Arcangeli, et al. "Focusing of 915 MHz Electromagnetic Power on Deep Human Tissues: A Mathematical Model Study, IEE Transactions on Biomedical Engineerings", Jan. 1984, pp. 47-52, vol. BME-31, No. 1.

Vythialingam Sathiaseelan, "Phase Steered Absorbed Power Optimization for Deep Heating Using the Annular Phased Array: A Theoretical Feasibility Study", Radiation Oncology Center Scientific Report, 1987-1988, pp. 322-327.

John W. Strohbehn, et al., "Optimization of the Absorbed Power Distribution for an Annular Phased Array Hyperthermia System", IG Radiation Oncology, Mar. 1989, pp. 589-599, vol. 16, No. 3.

V. Sathiaseelan, "Potential for patient-specific optimization of deep heating patterns through manipulation of amplitude and phase", Radiation Oncology Center, Mallinckrodt Institute of Radiology, Washington University School of Medicine, St. Louis, Missouri, USA, 1989, Strahlenther. Onkol. 165, pp. 743-745 No. 10.

R. J. Myerson, et al. "Phantom Studies and preliminary clinical experience with the BSD 2000", Int. J. Hyperthermia, 1991, pp. 937, vol. 7, No. 6.

P. Wust, "Strategies for optimized application of annular-phased-array systems in clinical hyperthermia", Int. J. Hyperthermia, 1991, pp. 157-173, vol. 7, No. I.

Alan J. Fenn, "Theory and Analysis of Near Field Adaptive Nulling", Conference Record of the Twentieth Asilomar Conference on Signals, Systems & Computers, Pacific Grove, CA, Massachusetts Institute of Technology, Lincoln Laboratory, Nov. 10-12, 1986, pp. 105-109.

Alan J. Fenn, "Evaluation of Adaptive Phased Array Antenna Far-Field Nulling Performance in the Near-Field Region", IEEE Transactions on Antennas and Propagation, Feb. 1990, pp. 173-185, vol. 38, No. 2.

J. Van Der Zee, et al. "Hyperthermia in Clinical Oncology 5th European BSD-Users Conference", Strahlenther.Onkol, 1991, pp. 46-61, vol. 167, No. 1.

Paul F. Turner and Theron Schaefermeyer, "Steerable Phased Arrays for Hyperthermia", 1326-IEEE/Ninth Annual Conference of the Engineering in Medicine and Biology Society, 1987, 3 pages, CH2513-0/87/0000-1326.

Paul F. Turner, "Regional Hyperthermia with an Annular Phased Array", IEEE Transactions on Biomedical Engineering, Jan. 1984, pp. 106-114, vol. BME-31, No. 1.

Paul F. Turner, "Hyperthermia and Inhomogenous Tissue Effects Using an Annular Phased Array", IEEE Transactions on Microwave Theory and Techniques, Aug. 1984, pp. 874-882, vol. MTT-32, vol. 8.

P.F. Turner, et. al., "BSD-2000 approach for deep local and regional hyperthermia: Physics and technology", 1989, pp. 738-741 Strahlenther.Onkol, vol. 165, No. 10.

* cited by examiner

DEEP HEATING HYPERTHERMIA USING PHASED ARRAYS AND PATIENT POSITIONING

FIELD OF THE INVENTION

The present invention relates generally to systems and apparatus for irradiating targets with electromagnetic radiation, and more specifically to systems having annular- or sector-type applicators and associated control systems for directing the application of electromagnetic radiation to selected regions within a target body.

BACKGROUND OF THE INVENTION AND RELATED ART

Several types of conventional and well-known therapeutic treatments for cancer in humans are in common use. These treatments include surgery, X-rays, radiation from radioactive sources, and chemotherapy, and are often combined in various ways to enhance treatment effectiveness.

Although such conventional treatment techniques have been successful in treating cancer in many patients and in prolonging the lives of many other patients, they are frequently ineffective against certain types of cancer and often have severe adverse side effects at the necessary treatment levels. Protracted treatment of cancer patients by X-rays or chemotherapy, as an illustration, tends to eventually destroy or inhibit the patients' natural immunological systems to an extent that many patients eventually succumb to common infectious diseases, such as influenza or pneumonia, which otherwise probably would not be fatal. Also, many patients having advanced stages of cancer or complications may become too weak to withstand the trauma of surgical or other cancer treatments; hence, the treatments cannot be undertaken or must be discontinued.

Due both to the prevalence and the typically severe consequences of human cancer, as well as frequent ineffectiveness of current treatments such as those mentioned above, medical researchers are continually experimenting in an attempt to discover and develop improved or alternative treatment methods for cancer.

Hyperthermia is the generation of artificially elevated body temperatures, and has received serious scientific consideration as an alternative cancer treatment. For instance, much research has been conducted into the effectiveness of hyperthermia alone or in combination with other treatment methods, and the promising results indicate that hyperthermia techniques appear to have the potential for being extremely effective in the treatment of many or most types of human cancers and without the often severely adverse side effects associated with current cancer treatments. Hyperthermia is sometimes called thermal therapy to indicate the raising of the temperature of a region of the body.

Researchers into hyperthermia treatment of cancer have reported that many types of malignant growths in humans can be thermally destroyed, usually with no serious adverse side effects, by heating the malignancies to temperatures slightly below that injurious to most normal, healthy cells. Furthermore, other types of malignant cell masses have reportedly been found to have substantially lower heat transfer to lessen the ability to dissipate heat, presumably due to poorer vascularity and reduced blood flow characteristics. These types of growths appear capable of preferential hyperthermia treatment since the vascularly-deficient malignant growths can be heated to temperatures several degrees higher than the temperature reached by the immediately surrounding healthy tissue. Consequently, it appears that different hyperthermia treatment protocols may allow hyperthermic treatment of those types of malignant growths which are no more thermally sensitive than normal tissue without destruction of normal cells, as well as the higher temperature, shorter hyperthermia treatment times of the more thermally sensitive types of malignancies which exhibit poor vascularity. This is usually an advantage for important medical reasons.

Researchers have further indicated that, as a consequence of these thermal characteristics of most malignant growths and the thermal sensitivity of normal body cells, hyperthermia temperatures for treatment of human cancer should be carefully limited within a relatively narrow effective and safe temperature range. Hyperthermia is generally provided by temperatures over 40 degrees C. (104 degrees F.). Hyperthermia treatment protocols have historically included temperatures well above 60 degrees C., but in recent years have generally been considered to include temperatures as high as 45 degrees C. (113 degrees F.). However, as there may be portions of a cancerous tumor that will exceed this level, the intent is to attempt to get as much of the tumor region above the 40 degree C. region as possible.

At treatment temperatures above the approximate 45 degrees C. (113 degrees F.), thermal damage to most types of normal cells is routinely observed if the time duration exceeds 30 to 60 minutes; thus, great care must be taken not to exceed these temperatures in healthy tissue for a prolonged period of time. Exposure duration at any elevated temperature is, of course, an important factor in establishing the extent of thermal damage to healthy tissue. However, if large or critical regions of the human body are heated into, or above, the 45 degree C. range for even relatively short times, normal tissue injury may be expected to result.

Historically, late in the last century alternating electric currents at frequencies above about 10 KHz were found to penetrate and cause heating in biological tissue. As a result, high frequency electric currents, usually in the megahertz frequency range, have since been widely used for therapeutic treatment of such common bodily disorders as infected tissue and muscle injuries. Early in this century, the name "diathermy" was given to this electromagnetic radiation (EMR) tissue heating technique, and several discrete EMR frequencies in the megahertz range have subsequently been allocated specifically for diathermy use in this country by the Federal Communications Commission (FCC).

The ability to do heat pattern steering permits energy to be focused and directed more selectively to the target tumor region. In order to provide sufficient heat energy to deep-seated target tumors, a lower frequency must be selected. This is because the penetration attenuation of human tissue increases at higher frequencies. As frequency is lowered however, the heating focus diameter increases. Thus, the proper frequency is needed to provide the optimum depth within acceptable heating pattern size limits. In general, hyperthermia is best applied when target tissue around the diseased area is also heated. This provides preheating of inflowing blood and reduces thermal conduction from the perimeter of the tumor to draw heat out of the tumor perimeter.

Current systems for applying electromagnetic radiation (EMR) to targets, such as living bodies and biological tissue, and for controlling the position of a region of heating within the target, typically include a plurality of electromagnetic radiation applicators powered by a multi-channel EMR system to provide heat pattern steering control through electronic phase and power steering. However, both the power and phase of the radiation output generated by each applicator must be controlled by a separate power channel of the EMR system to create the desired phased-array steering of heat pattern. Thus, an independent and individually-controllable power signal channel for each electromagnetic applicator is needed, which results in high system complexity and cost. Typically current systems require 4 or 12 independent EMR power signal channels to provide such electronic steering.

Some advanced hyperthermia EMR systems utilize multi-channel phased array systems that control frequency as well as the radiated power and relative phase. Each channel has electronic controls of power and phase and is connected to different antennas. The application of complex and expensive multi-channel amplifier systems to provide multiple EMR synchronous phase energy channels that have phase control to steer the heating region in the body allows electronic steering of the heating pattern, but at high cost and complexity which can make the treatment system cost prohibitive for routine clinical use.

Thus, there exists need for EMR applicator apparatus, and corresponding methods for EMR irradiation, which provide simplified heat pattern steering of EMR heating in a target, such as a target of biological tissue in a living body or tissue simulating matter.

SUMMARY OF THE INVENTION

In accordance with one representative embodiment described herein, a hyperthermia treatment system is provided for heating a selected region within a target body. The treatment system includes an electromagnetic radiation power source and a plurality of electromagnetic radiation applicators that are in electrical communication with the power source and arranged in a surrounding array around a focal region to concentrate their combined radiation output onto the focal region. The treatment system also includes a support mechanism that is adapted to support the target body within the surrounding array of applicators, and a positioning mechanism adapted to move the support mechanism and align the selected region within the target body with the focal region. Furthermore, the positioning mechanism is adapted to compensate for movement of the focal region in response to an interaction between the combined radiation output from the plurality of applicators and the target body.

In accordance with another representative embodiment described herein, a non-invasive hyperthermia treatment system is provided for heating a treatment region within a target body which includes an electromagnetic radiation power source and a plurality of electromagnetic radiation applicators in electrical communication with the power source, and which are arranged in a surrounding array around a focal region and aligned to concentrate a plurality of radiation outputs of substantially constant power and phase into the focal region. The treatment system also includes a support mechanism adapted to support a target body within the surrounding array of applicators, and a positioning mechanism adapted to move the support mechanism and supported target body in at least one plane orientated perpendicular to a longitudinal center axis of the surrounding array and to align the treatment region within the target body with the focal region. The positioning mechanism is further adapted to compensate for shifting of the focal region away from the longitudinal center axis in response to an interaction between the plurality of radiation outputs and the target body.

In accordance with yet another representative embodiment described herein, a method is provided for heating a selected region within a target body that includes the step of providing a plurality of electromagnetic radiation applicators in electrical communication with at least one electromagnetic radiation power source and arranged in a surrounding array around a focal region to concentrate the plurality of radiation outputs into a focal region, and wherein the power and phase output of each radiation output is substantially constant. The method also includes the steps of supporting a target body within the surrounding array of applicators, moving the support mechanism and supported target body in space relative to the focal region, and aligning the selected region within the target body with the focal region while compensating for a shifting of the focal region in space in response to an interaction between the plurality of radiation outputs and the target body. The method further includes the step of activating the plurality of electromagnetic applicators to heat the selected region within a target body.

BRIEF DESCRIPTION OF THE DRAWINGS

Features and advantages of the present invention will be apparent from the detailed description that follows, and when taken in conjunction with the accompanying drawings together illustrate, by way of example, features of the invention. It will be readily appreciated that these drawings merely depict representative embodiments of the invention and are not to be considered limiting of its scope, and that the components of the invention, as generally described and illustrated in the figures herein, could be arranged and designed in a variety of different configurations. Nonetheless, the present invention will be described and explained with additional specificity and detail through the use of the accompanying drawings, in which.

DETAILED DESCRIPTION OF EXEMPLARY EMBODIMENTS

Figure 1:
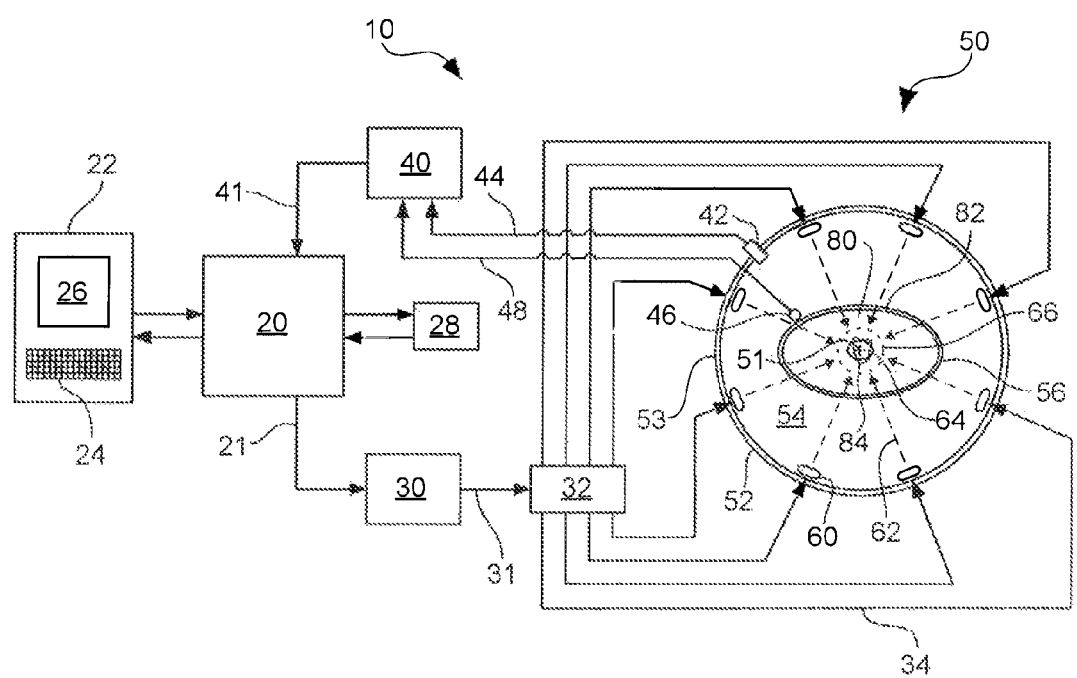
FIG. 1 is a schematic diagram of a hyperthermia treatment system and target body, in accordance with one representative embodiment.

The following detailed description makes reference to the accompanying drawings, which form a part thereof and in which are shown, by way of illustration, various representative embodiments in which the invention can be practiced. While these embodiments are described in sufficient detail to enable those skilled in the art to practice the invention, it should be understood that other embodiments can be realized and that various changes can be made without departing from the spirit and scope of the present invention. As such, the following detailed description is not intended to limit the scope of the invention as it is claimed, but rather is presented for purposes of illustration, to describe the features and characteristics of the representative embodiments, and to sufficiently enable one skilled in the art to practice the invention. Accordingly, the scope of the present invention is to be defined solely by the appended claims.

Furthermore, the following detailed description and representative embodiments of the invention will best be understood with reference to the accompanying drawings, wherein the elements and features of the embodiments are designated by numerals throughout.

Illustrated in FIGS. 1-16 are several exemplary embodiments of a hyperthermia treatment system which can be used for the treatment of a variety of diseases, such as cancer, and which embodiments also include one or more methods for deep-heating a selected region within a human or target body. As described herein, the hyperthermia treatment system provides several significant advantages and benefits over other devices and methods for thermally treating cancerous tumors or similar growths which may be found within a target body. However, the recited advantages are not meant to be limiting in any way, as one skilled in the art will appreciate that other advantages may also be realized upon practicing the present invention.

The hyperthermia treatment system can utilize a surrounding array of electromagnetic radiation (EMR) applicators, each providing an equal or substantially-equal emission of radiated energy, combined with variable patient positioning to create a desired deep-heating pattern or focal region substantially centered within the applicator array. In one representative embodiment, for instance, a power signal supplied to the EMR applicators by an EMR power source can be sub-divided so that the power and phase of the EMR emitted from each of the individual applicators, or antennas, is substantially equal and aligned to create a focal region at the center of the array. Specifically, the power supplied to the applicator array can be provided by a single high-power EMR source that is electrically coupled to a passive power splitting device, which in turn divides the power into a predetermined number of channels to power each of the EMR applicators in the surrounding applicator array. Controlling the position of the target body relative to the applicator array allows the selected region to be heated within the target body to be aligned with the focal region of the applicator array without the need for separate power conditioners or phase controllers for each applicator channel which would otherwise be required to electronically steer the focal region to coincide with the selected region of the target body to be heated.

The applicator array can be formed of a plurality of individual applicators or antennas for directing the EMR energy toward the target. As stated above, a single EMR power source can be coupled to one or more of the individual applicators, and can be controlled in both its amplitude and frequency output to control the power energy supplied to the electromagnetic radiation applicators and ultimately the temperature reached by the target tissue that is heated. Preferably, all of the applicators are primary antenna radiators coupled to the EMR power source through a passive power splitter and activated to radiate electromagnetic radiation of approximately equal amplitude and frequency (e.g. power), and phase. The dimensions and characteristics of the focal region created by the concentrated radiated energy can be determined both by test results and by numerical models which predict the interactions between the intersecting beams of radiated energy.

The use of variable body positioning within the applicator array of the simplified hyperthermia treatment system described herein can provide for phased array control of heating patterns in predictable steering positions in a target at a lower cost and reduced complexity, leading to a simplified annular applicator apparatus for EMR heating for any required purpose, such as medical hyperthermic treatment of cancer or of other medical uses or research.

FIG. 1 shows a block diagram of a system 10 for creating hyperthermia in a target body 80 by means of electromagnetic radiation (EMR), in accordance with an exemplary embodiment. A central processor unit 20 can be used to control the hyperthermia treatment system 10, and can be connected in an interactive feedback relationship with each of its elements, including a control panel 22, an EMR power source 30 which provides the EMR power to a surrounding array 50 of EMR applicators 60, and a monitoring unit 40 which can accept a plurality of inputs including, but not limited to, the position of the target body 80, the temperature distribution throughout the target body, and the strength and distribution of an electric field created by the plurality of EMR applicators 60, etc.

For example, in one aspect the monitoring unit 40 can accept inputs 44 from displacement detectors 42 which indicate the real-time position of the target body relative to the geometric center 66 of the array of EMR applicators 60. The displacement detectors can employ a variety of technologies to measure a perimeter location of the target body, a center location, or both. In another aspect the monitoring unit 40 can also accept inputs 48 from electric field detectors 46 which indicate the real time electric field (or E-field) amplitude at selected locations. These detectors 46 can be positioned against or close to the outer surface 82 of the target body 80. A plurality of E-field detectors 46 can be used, preferably at least about four, and can be represented diagrammatically by a single input 48 into the monitoring unit 40. The E-field detectors 46 can provide feedback to the CPU 20 of the relative amplitude balance of the EMR incidental to the target surface.

A control panel or console 22 can be coupled to the CPU 20 and used by an operator to both control a treatment cycle and monitor its progress. The control panel 22 can be used to display any information obtained from the target 80 as well as all indicators of system operation on a display 26. The control panel 22 can also be used to receive operator input or commands through an input device 24, such as a computer keyboard or mouse pointing device.

Various memory devices, represented by a single memory block 28, can also be coupled to the CPU 20. The memory 28 can store the result of pretreatment calculations which are used by the CPU 20 to control the progress of the treatment. Also, all pertinent operating data can be stored in another part of the memory 28 as generated in order to have a complete record of the treatment process and results for future use.

The hyperthermia treatment system 10 includes at least one high-frequency EMR energy power source 30 that is coupled to and controlled by the CPU 20. The power source 30 is in turn coupled to a power splitter 32 which divides the EMR energy into a plurality of channels (e.g. such as conductive co-axial cables 34), with each channel carrying a power signal having substantially the same frequency, phase and amplitude, and which can be coupled to an individual EMR applicator 60. As can be seen in FIG. 1, in one aspect eight individual EMR applicators 60 can be arranged together in an octagonal or circular array 50 that surrounds an ellipsoidal target body 80, which can be understood to represent a cross-section of a torso or body part of a human patient.

Each EMR applicator 60 is diagrammatically represented in FIG. 1 by a rounded oval shape. In reality, however, each applicator 60 can have a shape suitable for the emission of microwave EMR, such as the flat dipole antenna pair shown in FIGS. 2-3. Furthermore, it is to be appreciated that FIG. 1 is a two-dimensional representation of a three-dimensional phenomena, with both the radiators 60 and target body 80 extending for some distance perpendicular to the plane of the drawing. The radiation output 62 emitted from each applicator 60 can be aligned so that the E-field component is perpendicular to the plane of the drawing. The dashed arrows approximate the converging geometry of the plurality of EMR outputs 62 emitted by the various applicators 60, and which are concentrated into a combined radiation output or focal region 64 that can be substantially centered in the applicator array 50.

As the radiation outputs 62 emitted by the multiple applicators 60 converge on the focal region 64, the E-fields of the EMR beams are lined up so that the target body 80 sees a converging, approximately circular wave front 66. The energy of the various EMR outputs converges in the focal region 64, which is where the electric field (hereinafter "E-field") components can add constructively and heat the selected region 84 of the target 80 to a greater degree than that caused by any one EMR applicator 60 alone. Moreover, this improved deep internal heating can be affected without dangerously increasing the radiant energy density at the outer surface 82 of the target body 80, as the incoming energy is normally spread equally over the target's entire outer surface. Thus, the energy imparted to the target 80 is concentrated near the selected region 84 inside the target body, where it is desired, and minimized to the greatest extent possible at the outer surface 82 and at other intermediate locations within the target body.

As described above, the energy radiated by each EMR applicator 60 can have a constant phase relationship with that emitted by the other applicators, which can create a synergistic result in the focal region 64 of the applicator array 50 whereby the selected region 84 of the target body 80 is heated to a degree greater than that of a simple sum of the energy of the various applicators 80. Furthermore, with all of the EMR applicators operating precisely in phase, the focal region 64 can be symmetrical around the center longitudinal center axis of the applicator array 50.

As will be understood by one of skill in the art, the relative power density at each point within the surrounding array 50 is proportional to the square of the E-field, and can experience a relatively sharp peak in the focal region 64 in a non-attenuating medium such as air or water. Moreover, the heating at any given point is due to the power absorbed at that location, which in turn is directly proportional to the power density at that same location. Since the power density is proportional to the square of the E-field, a simple additive increase in the electric field at a given point results in an increase in the power density by the square of the electric field. Thus, when multiple EMR applicators 60 are installed and aligned in the surrounding array 50, the increase in power density can be much greater than that provided by simply increasing the power output of a single EMR applicator.

By way of illustration, the E-field in a focal region resulting from two applicators is twice what would be caused by a single applicator, while the power density is $2^2=4$ times greater. Similarly, when eight applicators 60 are used, as shown in FIG. 1, the E-field at the center is eight times and the power density at the focal region is $8^2=64$ times greater than the power density caused by a single applicator. It is advantageous that this increase in the power density in the selected region 84 of the target body 80 can be obtained without significantly increasing the power density at any one point on the outer surface 82 of the target body. Furthermore, it is contemplated that this synergistic result stems from all of the EMR applicators operating at a substantially identical frequency and with aligned phase relationships so as to create constructive addition of the multiple beams 62 of electromagnetic radiation that allows deep heating of the target body 80 without the undesired heating of the intermediate portions and surface portions 82.

The above discussion can apply to non-lossy targets in which there is no energy absorption by the medium, and the amplitude of the EMR from any given applicator 60 is undiminished as the radiation passes through the target body. It will be appreciated by one of skill in the art, however, that any medium capable of absorbing the radiant power, such as the living tissue inside the human target body 80, may also be attenuating and can substantially reduce the central power density peak at the selected region 84 while increasing the power density at the surface 82 and intermediate portions of the target body. Consequently, with actual lossy target bodies 80 the amplitude of the E-field at the selected region 84 inside the target body 80 can typically be approximately ½ the E-field amplitude at the outer surface 82. For the case of eight applicators 60, therefore, the power density in the selected region 84 is approximately $8^2/7^2$, or approximately 1.3 times that at the target body surface 82. It is important to note, however, that the power density in the selected region 84 is still sixty-four times that which would be caused by a single applicator 60 alone.

The above-described synergistic increase in power density in the focal region 64 can be created when each of the EMR applicators 60 radiates at substantially the same frequency and phase to align the E-fields of the emitted EMR output into constructive addition. Moreover, this in-phase alignment of the various emitted E-fields can occur along the longitudinal center axis 51 of the applicator array 50, which axis is perpendicular to the page in FIG. 1. If the various applicators 60 radiate energy at slightly different frequencies or phases, the various E-fields may not always add constructively, and the power density enhancement described above may not occur. In such circumstances the power density in the focal region 64 may be reduced to the simple sum of the individual power densities. It is therefore desirable for the frequency and phase of the electromagnetic radiation emitted by all applicators 60 be substantially identical and correctly aligned.

For this reason, in one representative embodiment the hyperthermia treatment system 10 utilizes a single EMR power source 30 and a power splitter 32, so that the power supplied to each applicator 60 has the same frequency and phase. While it is possible to use multiple sources providing that they can be precisely frequency-locked to emit identical frequencies, the practical considerations to accomplish this may complicate the system and add expense with little benefit. Thus, a preferred configuration can utilize only a single EMR power source 30 and power splitter 32. It is not necessary, however, that the frequency supplied to the EMR applicators 60 be invariant with respect to time, and in certain situations it can be desirable for the EMR power source 30 to provide a controllable frequency that may be adjusted to optimize performance with respect to the various types of tissue found within a non-homogeneous living target body 80.

It may also be appreciated that the length of the cables 34 coupling the power splitter 32 to the EMR applicators 60 can affect the arrival time, and therefore the phase, of the powering signals which drive the applicators. Consequently, each EMR power cable 34 can be provided in a predetermined length configured so that the emitted EMR outputs from'the different applicators constructively interfere with each other as they converge together in the focal region. Cables 34 supplying a symmetric applicator array (such as the circular array 50 and housing 52 shown in FIG. 1), for example, can have approximately equal lengths for supplying approximately equal phases, while EMR power cables 34 supplying a non-symmetric array (such as an octagonal or oval applicator array and housing (not shown)) can have different predetermined lengths, with each being adapted to supply their respective EMR applicator 60 with a phase-tuned EMR power signal that results in the multiple EMR outputs interfering constructively with each other as they combine in the focal region.

The shape and location of the focal region 64 can be determined by the distribution of the EMR applicators 60 in operation, the relative phase between them, and the frequency of the EMR output. It has been determined that the use of four or more uniformly spaced radiating EMR applicators 60 will provide an approximately circular (ellipsoidal in three dimensions) focal region 64. Nevertheless, eight EMR applicators 60 are used in the surrounding applicator array 50 shown in FIG. 1 instead of four, because it has also been determined that the power density, and thus heating, at the surface 82 of the target body 80 is more uniform than when only four radiating applicators are used. An increase in the number of applicators 60 above eight when placed in a single dipole ring does not appear to make a material difference in the operation of the hyperthermia treatment system 10.

The EMR applicator array 50 can be surrounded and supported by an open-ended cylindrical housing or casing 52 made from a low dielectric constant material such as plastic, and which serves to support the individual applicators 60 in place while decreasing any hazardous stray radiation. As shown in FIG. 1, a target body 80 can be inserted through one or both of the open ends of the casing 52 and suspended interiorly of the applicator array 50. Furthermore, the target body 80 can be surrounded by a high dielectric constant fluid-filled bolus 54 which, in one aspect, contains deionized water. The bolus 54 can be made from a thin and flexible dielectric sheet or membrane having a conformable interior contact surface 56 which can seal tightly around the outer surface 82 of the target body 80. The EMR applicators 60 can have a size and length that efficiently radiates EMR output into the high dielectric constant fluid-filled bolus 54 as compared with the housing 52 and the surrounding air space.

The use of a bolus 54 can provide several important advantages. For example, the fluid therein can be circulated through an external heat exchanger (not shown) to cool the outer surface regions 82 of the target during treatment. Additionally, there is very little power loss in a bolus 54 filled with deionized water, so that substantially all of the power radiated by the EMR applicators 60 can be delivered to the target body 80. As stated above, the electrical length of the EMR applicators 60 or antenna is such that it is an inefficient radiator into the low dielectric surrounding air and an efficient radiator into the fluid-filled bolus 54 due to the much longer radiating wavelength in the surrounding air.

Use of the fluid-filled bolus 54 can also improve the impedance match between the applicators 60 and the target body 80. At the frequencies of interest, the impedance of a typical biological target 80 is approximately forty-four ohms. The impedance of the applicators 60 and other electrical portions of the system can preferably be about fifty ohms in order to be compatible with standard components, and the impedance of deionized water at the frequencies of interest can also be approximately forty-four ohms, so that all parts of the hyperthermia treatment system 10 can be inherently closely matched. It may be appreciated that if the water-filled bolus 50 were not present, a large mismatch would occur at the radiating face of the applicators 60 and at the outer surfaces 82 of the target body because the impedance of air is approximately that of free space, or three hundred seventy-seven ohms. Moreover, any impedance mismatches can result in reflections at the boundaries which operate to both lower the percentage of radiated energy delivered to the target body 80 and increase stray radiation hazards.

Figure 2:
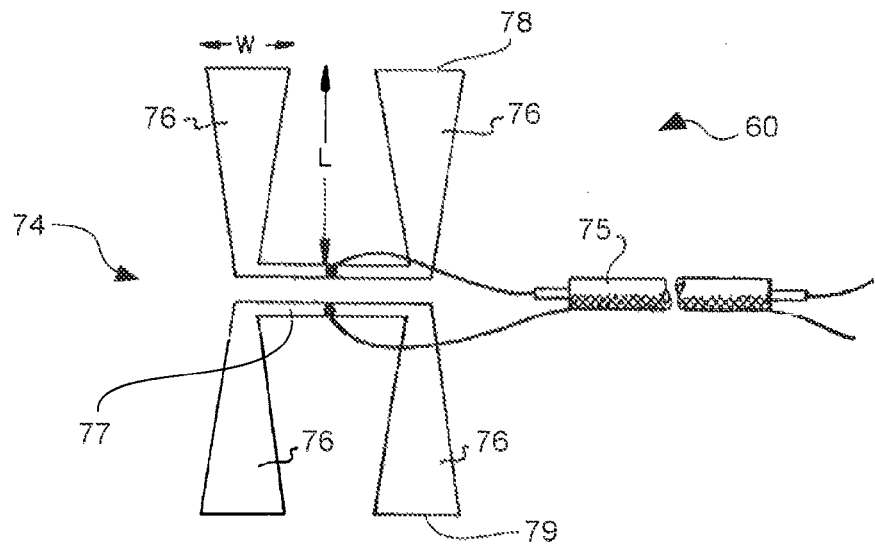
FIG. 2 illustrates a dipole antenna pair for use with the hyperthermia treatment system FIG. 1.

A representative EMR applicator 60 suitable for use with the present system 10 is shown in FIG. 2. In one aspect the applicator can be a dipole antenna pair 74 sized for use with EMR of the frequencies contemplated. Each arm 76 of the upper radiating portion 78 and the lower radiating portion 79 can act together to form a dipole pair radiator commonly called a "dipole couplet". In addition, a coaxial feed line 75 can be coupled to the center of the upper and lower joining sections 77 to feed energy to the upper and lower radiating portions 78, 79, respectively. The joining sections 77 between the arms 76 can be parallel strips (as shown) or other types of electrical connections, such as coaxial or twisted pair conductors. When the dipole antenna pair 74 is driven in a conventional manner, the E-field of the emitted radiation can be aligned with the length of the arms 76.

It is known that the shape and size of the antenna arms 76 can determine the optimum frequencies of operation and impedance characteristics of the dipole-pair EMR applicator 74. It has been determined experimentally that a dipole 74 having tapered arms, wherein the ratio of arm width (W) to length (L) is maintained constant at approximately 0.087, gives a good impedance match with the remainder of the system 10. When the dipole-pair applicators 74 are placed parallel and spaced apart when combined into a cylindrical array 70 (as shown in FIG. 3) and joined with a common transmission line 75 (as shown in FIG. 2), and a water bolus as similar to that discussed with FIG. 1 is used, an impedance match of about fifty ohms can be achieved on the common feed coaxial line 75.

Figure 3:
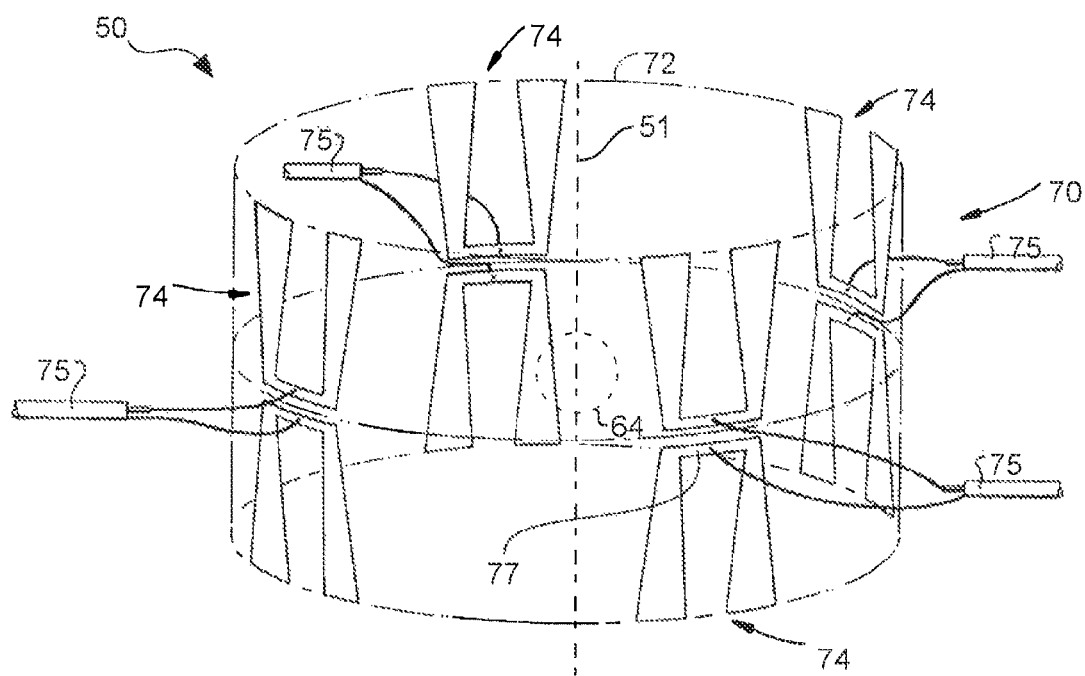
FIG. 3 illustrates a surrounding array of four dipole antenna pairs for use with the hyperthermia treatment system of FIG. 1.

Referring now to FIG. 3, in one representative embodiment of the applicator array 50 generally illustrated in and described with reference to FIG. 1, four dipole-pair EMR applicators 74 can be assembled around a rigid, non-conducting frame 72 to form a cylindrical applicator array 70. Each dipole-pair applicator 74 can be separately connected to the EMR power source and power splitter through a separate coaxial feed line 75 and operated to direct microwave EMR towards a focal region 64 located in the center of the array 70 and about a longitudinal center axis 51, and where the target specimen (not shown) is to be subsequently positioned. Preferably, a de-ionized water bolus (also not shown) surrounds the target so as to better couple energy from the applicators 74 to the target, and to minimize reflections.

As described above, the simplified EMR system can include the EMR power source, the power splitter, the various co-axial feed lines 75 and dipole-pair EMR applicators 74 arranged around frame 72 to form the cylindrical applicator array 70, and can be configured so that the frequency and phase of the radiation emitted by each of the EMR applicators 74 are substantially identical and aligned, respectively. In one aspect the arms of the applicators 74 can be placed inside and surrounded by the water inside the bolus, while the joining sections 77 connecting each pair of arms to form the dipole couplets can pass through water-tight fittings to be located outside the water bolus and along the outside of the rigid, non-conducting frame 72.

It is also to be appreciated that additional types of EMR applicators can be used to heat the target body. These can include, but are not limited to, horn type radiators, patch radiators, dipole antennae, folded dipoles, monopoles, and waveguides, etc. Furthermore, the antenna sources may also be linearly polarized to provide for the greatest enhancement of the heating in the overlapping focal region.

FIGS. 4-11 are schematic diagrams of another representative embodiment of the simplified hyperthermia treatments system 100 which illustrate additional aspects and details of the surrounding array 110 of electromagnetic radiation (EMR) applicators 120 that also includes a fluid-filled bolus 130 and a target body 140. It is recognized that the other components of the hyperthermia treatment system described above, such as the CPU, the controller interface, the EMR power source, the power splitter and the monitoring device, etc., and which are not shown in FIGS. 4-11 are nevertheless included components of the treatment system 100 which can operate to power, monitor and position each of the EMR applicators 120, the target body 140 and the support mechanism 150, respectively.

Figure 4:
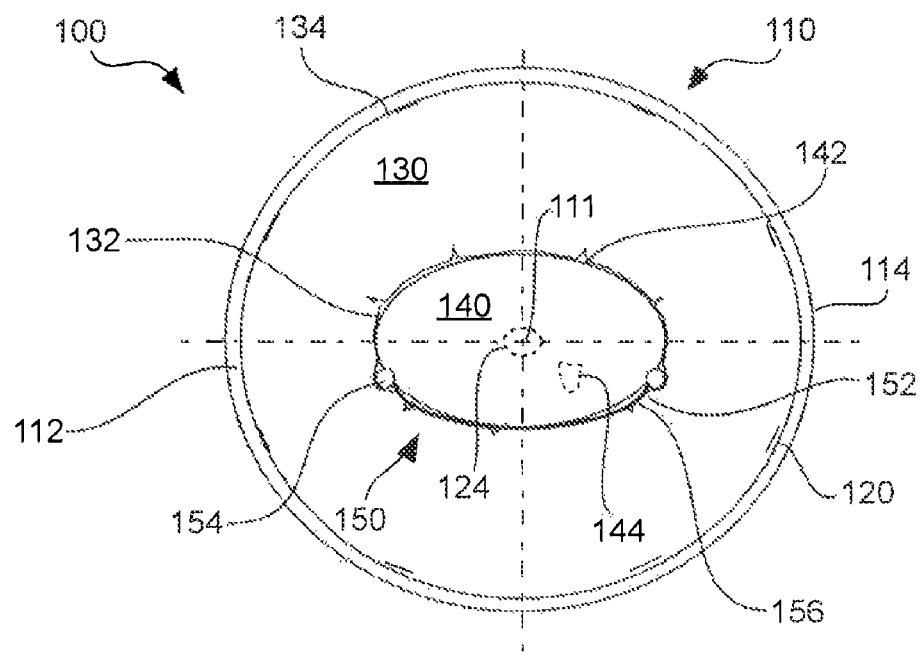
FIG. 4 is a schematic diagram of a surrounding array of electromagnetic radiation applicators, a target body and a support mechanism, in accordance with another representative embodiment.

Referring now to FIG. 4, eight individual EMR applicators 120 can be arranged together in an octagonal or circular array 110 that surrounds the ellipsoidal target body 140, which can be understood to represent a cross-section of a torso or body part of a human patient. The EMR applicator array 110 can be surrounded and supported by an open-ended non-electrically conductive cylindrical casing or housing 112, which serves to support the individual applicators 120 in place. The housing 112 can comprise a low dielectric material, such as a molded thermoplastic or similar synthetic substance, to provide structural support and to reduce the amount of energy coupled to the outer air space.

Although the EMR applicators 120 are diagrammatically represented in FIGS. 4-11 by straight lines, it is to be appreciated that each applicator can have a shape and configuration suitable for the emission of microwave EMR, some of which have been described above. EMR power can be supplied to the applicators by one or more EMR power sources and sub-divided so that the power and phase of the EMR emitted from each of the individual EMR applicators, or antennas, is substantially equal and aligned to create a focal region 124 which can be symmetrical around the longitudinal center axis 111 of the applicator array 110. As described above, the energy radiated by each EMR applicator 120 can have a constant phase relationship with that emitted by the other applicators to create a synergistic, constructive interference effect in the focal region whereby the selected region 144 of the target body 140 is heated to a degree greater than that of a simple sum of the energy of the various applicators 120.

The target body 140 can be inserted through one or both of the open ends of the casing 112 and surrounded by a fluid-filled bolus 130 which, in one aspect, contains de-ionized water. The bolus can be made from a thin, flexible dielectric sheet or membrane having a conformable interior contact surface 132 which can seal tightly around the outer surface 142 of the target body 140. Moreover, an outer surface 134 of the bolus 130 can contact the EMR applicators that are spaced around the inside surface of the housing 112 so as to directly couple the emitted EMR radiation from the EMR applicators directly into the target body. Also shown in FIG. 4, the target body 140 can be suspended within the applicator array 110 and bolus 130 on a support mechanism 150. In one aspect the support mechanism can comprise a sling 152 having a sheet 156 of flexible material that is stretched between two axially-extending support bars 154. The target body can be suspended on the flexible sheet 156, which in turn can conform to the contours of the lower portions of the target body as needed. The flexible sheet 156 can also be formed from a material, such as cloth, that is substantially transparent to the EMR emitted by the applicators 120, so as to not block and impede the transmission of the EMR energy from the applicators located below target body 140 and support mechanism 150.

Figure 5:
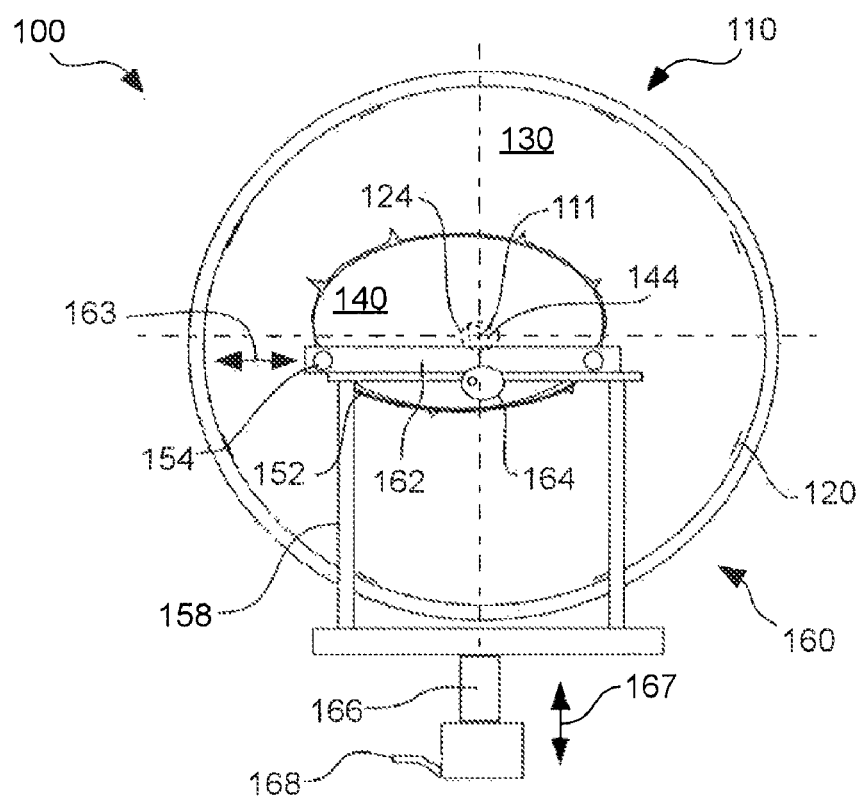
FIG. 5 is a schematic diagram of the applicator array, target body and support mechanism of FIG. 4 with a positioning mechanism, in accordance with a representative embodiment.

Referring now to FIG. 5, the sling 152 and suspended target body 140 can extend through the interior of the cylindrical applicator array 110 to be supported or positioned at one or both ends with a frame or pedestal 158. Moreover, a positioning mechanism 160 adapted to move the support mechanism 150 and supported target body 140 can be incorporated into one or both pedestals 158 so as to move the support mechanism and supported target body in at least one plane that is orientated perpendicular to the longitudinal center axis 111 of the applicator array and align the select treatment region 144 within the target body 140 with the centralized focal region 124 of the EMR applicator array 110.

For instance, in one aspect the positioning mechanism 160 can include a horizontal-positioning component 162 which moves the ends of the two axially-extending support bars 154 back and forth along a horizontal axis 163 that is perpendicular to the longitudinal center axis 111 of the applicator array 110. The horizontal positioning component 162 can include a horizontal driver device 164, such as hand crank, which can be a manually-operated to move the support mechanism. Other horizontal driver devices 164 that can be either manually-operated or controlled with the CPU to activate the horizontal positioning component 162 are also contemplated and can include, but are not limited to, hydraulic drives, pneumatic drives, electric-motor drives and mechanical gear drives, etc., and combinations thereof.

The positioning mechanism 160 can further include a vertical-positioning component 166 which moves the ends of the two axially-extending support bars 154 up and down along a vertical axis 167 that is perpendicular to the longitudinal center axis 111 of the applicator array 110. The vertical positioning component 166 can also include a vertical driver device 168, such as foot crank, which can be manually-operated to move the support mechanism. Other vertical driver devices 168 that can be either manually-operated or controlled with the CPU to activate the vertical positioning component 166 are also contemplated and can include, but are not limited to, hydraulic drives, pneumatic drives, electric-motor drives and mechanical gear drives, etc., and combinations thereof.

As a result, the positioning mechanism 160 of the simplified hyperthermia system 100 can provide the variable patient positioning capability that permits predictive targeting and placement of the body and enables the deeply-focused energy pattern 124 to be directed to the targeted tissues in the deep selected region 144 to be heated. In one aspect the positioning mechanism 160 can position the target body both in anterior (up) and posterior (down) positions as well as right and left positions relative to the longitudinal center axis of the applicator array 110, allowing for central steering of the deep focus EMR energy in accordance with a wide variety of targeted energy steering patterns and protocols. In another aspect the positioning mechanism can also move the target body forwardly and rearwardly along the longitudinal center axis 111 of the applicator array 110.

In yet another aspect the positioning mechanism 160 can be incorporated into both pedestals 158 supporting either end of the support mechanism 150 and can operate in unison to maintain a constant attitude of the target body 140 relative to the longitudinal center axis 111 of the applicator array 110, or can be moved separately or in opposite directions, etc., to rotate and adjust the angular orientation of the target body relative to the longitudinal center axis 111.

It is understood that, prior to the commencement of treatment, the location of the targeted tissues in the selected region to be heated can be predetermined relative to a set of perimeter reference points or center reference points on the target body 140. Measuring the position of these same reference points relative to the longitudinal center axis 111 of the array 110 of EMR applicators 120 can be useful in prepositioning and aligning the selected region 144 of the target body 140 with the focal region 124 before activation of the EMR applicators. Therefore, as illustrated in FIGS. 6-9, the simplified hyperthermia system 100 may also include a displacement measurement system 170 which can be used to monitor the real-time position of the target body 140 relative to the longitudinal center axis 111 of the array 110 of EMR applicators 120. The displacement measurement system 170 can further comprise one or more displacement detectors, each of which can utilize any one of a number of measurement methods or technologies to collect positional measurements of the target body, such as a perimeter location of the outside surface 142 of the target, or a center location, or both.

Figure 6:
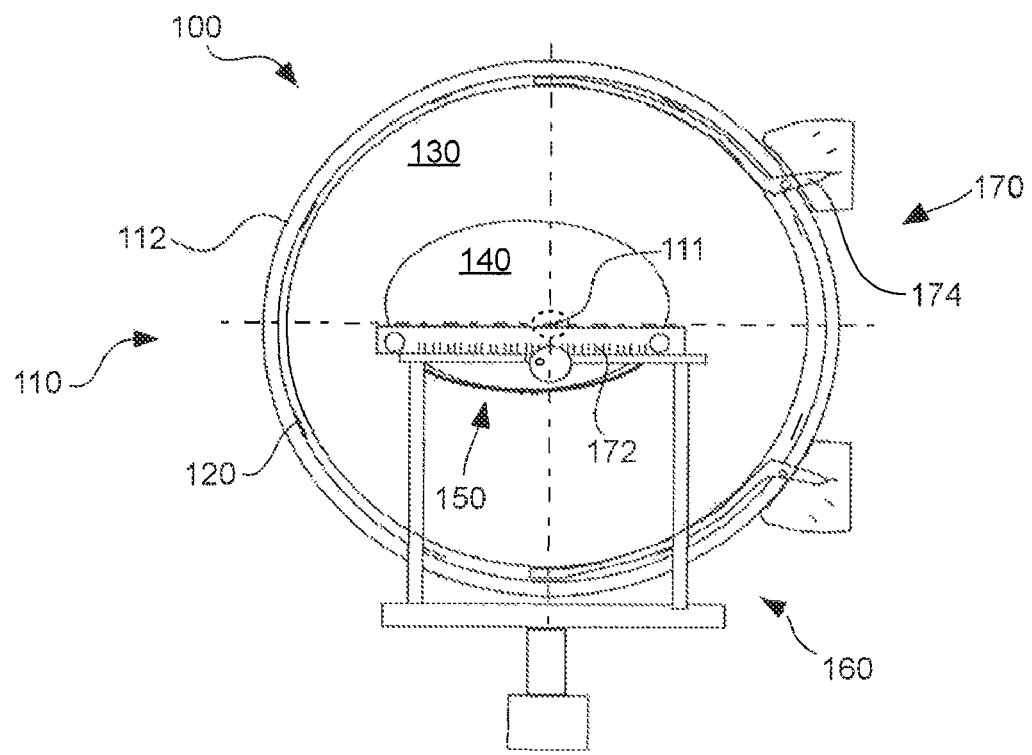
FIGS. 6-7 together illustrate a schematic diagram of the applicator array, target body, support mechanism, positioning mechanism and a displacement measurement system, in accordance with another representative embodiment.
Figure 7:
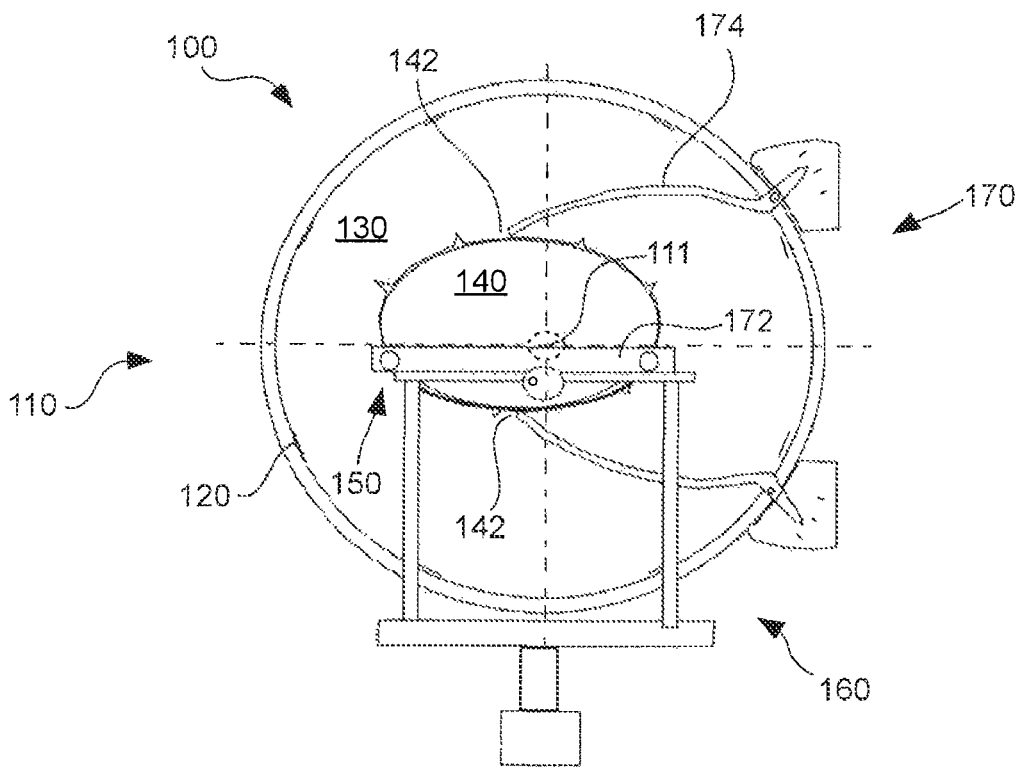

In one aspect shown in FIGS. 6-7, the displacement measurement system 170 can include one or more horizontal displacement detectors 172, such as a mechanical scale, which can be used to visually measure the horizontal displacement of the support mechanism 150 and/or the suspended target body 140 from an initial centered position to provide, among other things, a direct mechanical measurement of the horizontal displacement of the support mechanism 150 and/or the suspended target body 140. The displacement measurement system 170 can also include one or more vertical displacement detectors 174, such as pivoting mechanical rulers/sensor rods, that can be used to contact and measure both the top and bottom reference points on the outer surface 142 of the target body and from thence provide another direct mechanical measurement (e.g. the vertical displacement of the suspended target body from an initial centered position). Shown outside the fluid-filled bolus 130 in FIG. 6, one or both of the sensor rods can optionally extend inside the water bolus space, as illustrated in FIG. 7, to allow for an accurate measurement from the central portion of the dipole array and the body, while having a water-sealed flexible passage through the plastic support tube or housing 112 to prevent water from leaking out from the bolus.

Other types of displacement detectors can also be used to either visually measure or electronically measure the horizontal and/or vertical locations of the various reference points, and can include, but are not limited to, electronic scales, dielectric contact bars and linear differential voltage transformers (LVDT's), etc., and combinations thereof.

Figure 8:
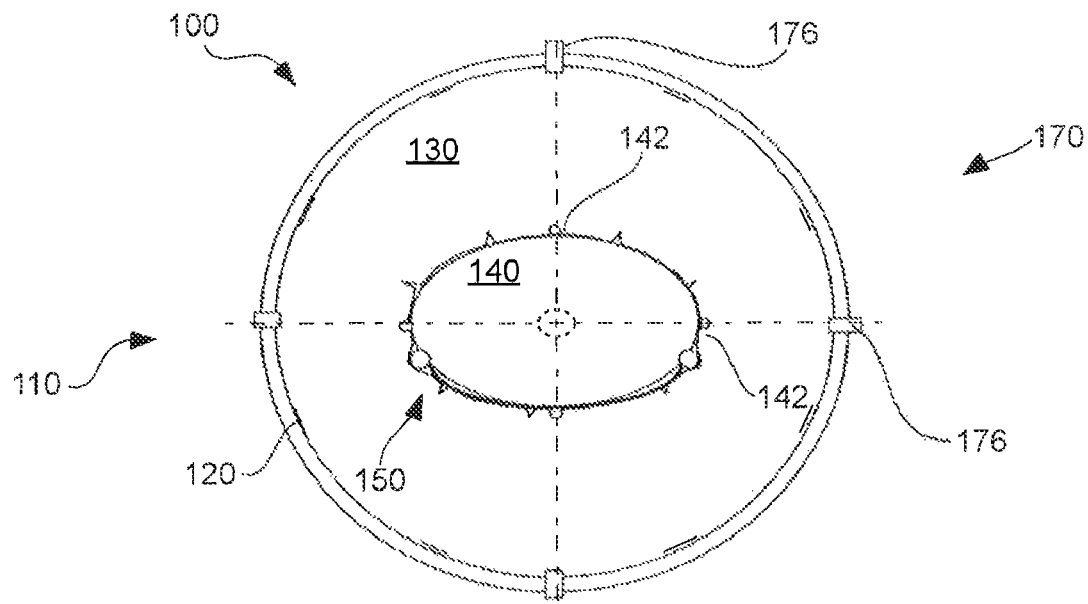
FIGS. 8-9 together illustrate a schematic diagram of the applicator array, target body, support mechanism and a displacement measurement system, in accordance with yet another representative embodiment.
Figure 9:
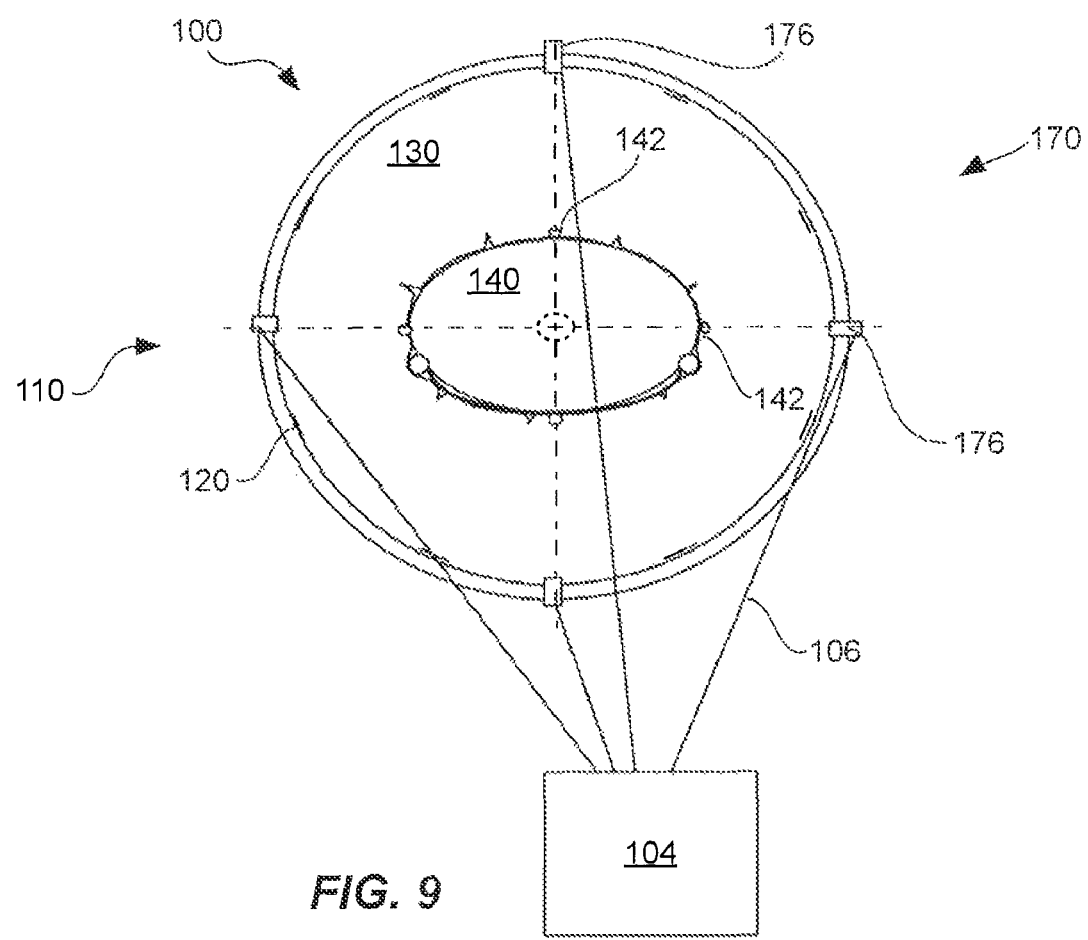

In another embodiment of the hyperthermia treatment system 100 shown in FIGS. 8-9, the displacement measurement system 170 can employ a plurality of non-contacting displacement detectors 176, such as ultrasound distance monitoring and laser distance monitoring, that measure a distance through the water bolus 130 from the housing 112 to one or more horizontal and vertical reference points on the outer surface 142 of the suspended target body 140. These non-contacting measurements are possible because of the significant reflection between the fluid within the bolus and that body for both the ultrasound signal transmitted to the body through the water and a laser light signal being transmitted through the transparent water to the target body surface. Furthermore, these non-contacting measurements can be conducted in the real-time and can be used to verify any ongoing positional adjustments of the target body by the positioning mechanism.

From these positional measurements the actual horizontal and vertical displacements of the target body relative to an initial centered position can be calculated. In one aspect an array of non-contacting position detectors 176 can be mounted into the housing 112 and merged with the surrounding array 110 of EMR applicators to form a combined hyperthermia treatment system which can advantageously measure the position of the target body 140, and thus the selected region 144 within the target body, simultaneous with the application of the hyperthermia treatment with the EMR applicators. As shown in FIG. 9, the non-contacting displacement detectors 176 can also be electronically coupled to a monitoring unit 104 with a plurality of displacement sensor cables 106, and which monitoring unit can in turn be electronically coupled to the CPU (not shown).

Figure 10:
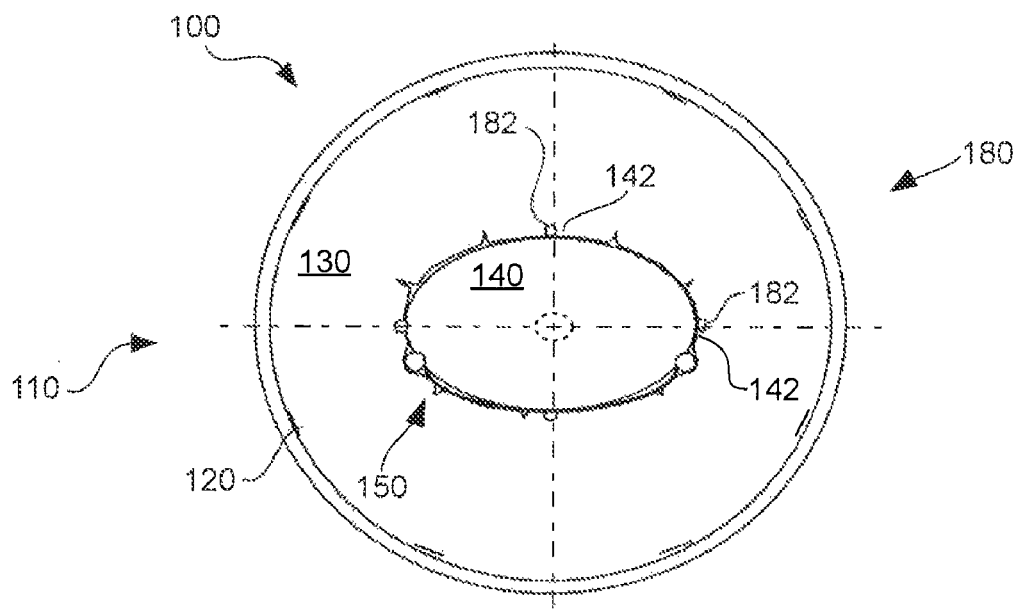
FIGS. 10-11 together illustrate a schematic diagram of the applicator array, target body, support mechanism and a radiated energy measurement device, in accordance with yet another representative embodiment.

In addition to the capabilities described above for monitoring and observing the real-time position of the target body 140, in certain situations it may also be useful to continuously observe and record the distribution of the E-field outside the body during hyperthermia treatment, by reason of the target body having lossy characteristics which interact with and affect the distribution of the E-fields emitted by the plurality of EMR applicators, as described above. Real-time measurements of the E-field can thus be used to monitor and record the shifting of the heating pattern which can result from the positional changes in the target body 140 resulting from operation of the positioning mechanism 160. Thus, as shown in FIGS. 10-11, the simplified hyperthermia system 100 may also include an E-field measurement system 180 which can be used to monitor the strength of the E-field in real time and at various locations near the outer surface 142 of the target body 140.

In one aspect, for instance, the E-field measurement system 180 can include a plurality of E-field detectors 182 positioned at spaced-apart locations immediately adjacent the outer surface 142 of the target body 140. The E-field detectors can be of the type previously disclosed in U.S. Pat. No. 4,638,813 by one of the present inventors, and which is incorporated by reference in its entirety herein. However, other types of sensors or detectors known in the art for monitoring the E-field inside an array 110 of EMR applicators 120 are also contemplated and may be considered to fall within the scope of the present invention.

Figure 11:
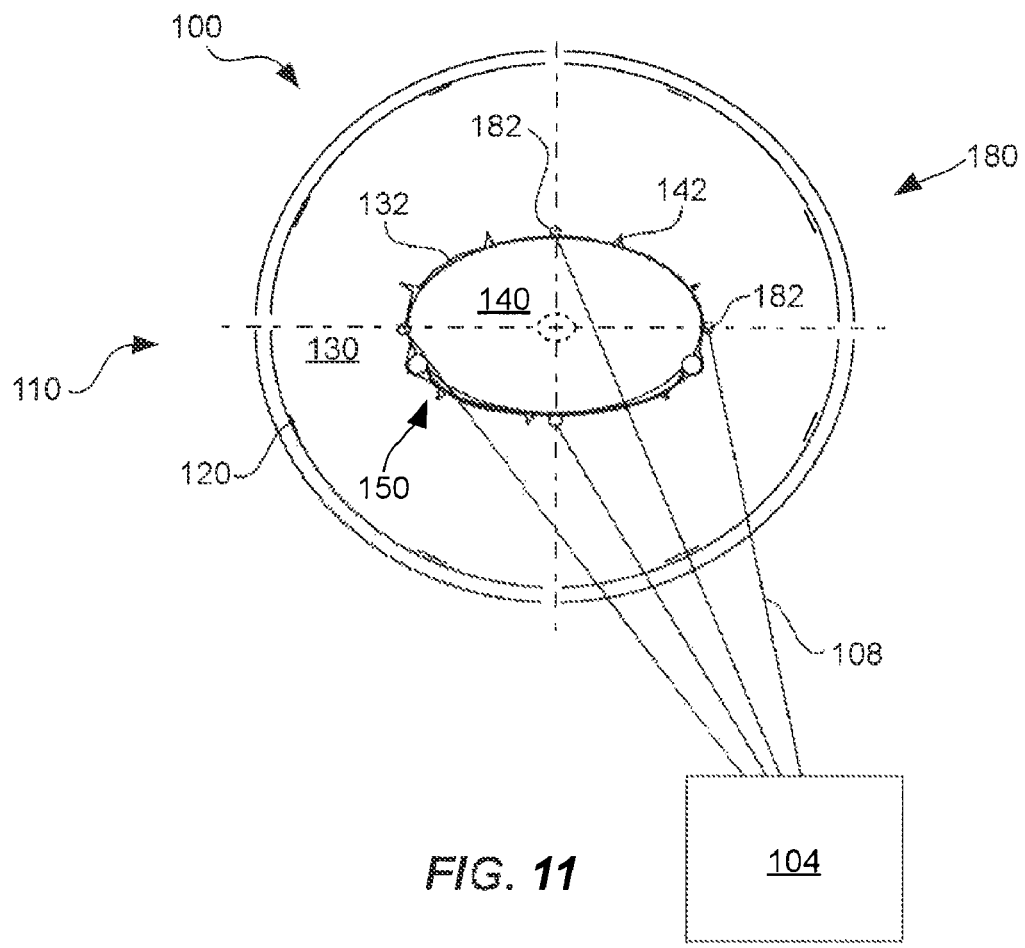

Also shown in FIG. 11, the E-field detectors 182 can be electronically coupled to the monitoring unit 104 with a plurality of E-field sensor cables 108 extending out through the fluid-filled bolus if located inside the fluid-filled volume, or out from between the outer surface 142 of the target and the interior contact surface 132 of the bolus 130 if located at the interface. It is also possible that the E-field detectors 182 could be attached to the inside of the interior contact surface 132 of the bolus membrane 130 and pass separately through the plastic wall outside of the water-filled area with separate and direct connections 108 to the monitoring unit 104.

Although the monitoring unit 104 is shown in FIGS. 9 and 11 as receiving measurement inputs from either the displacement measurement system 170 or from the E-field measurement system 180, it is recognized that other configurations for receiving and converting the various measurement inputs into data useful for recording and analysis are possible, including separate and distinct monitoring systems for each type of measurement detector, and which can also be considered to fall within the scope of the present invention.

Figure 12:
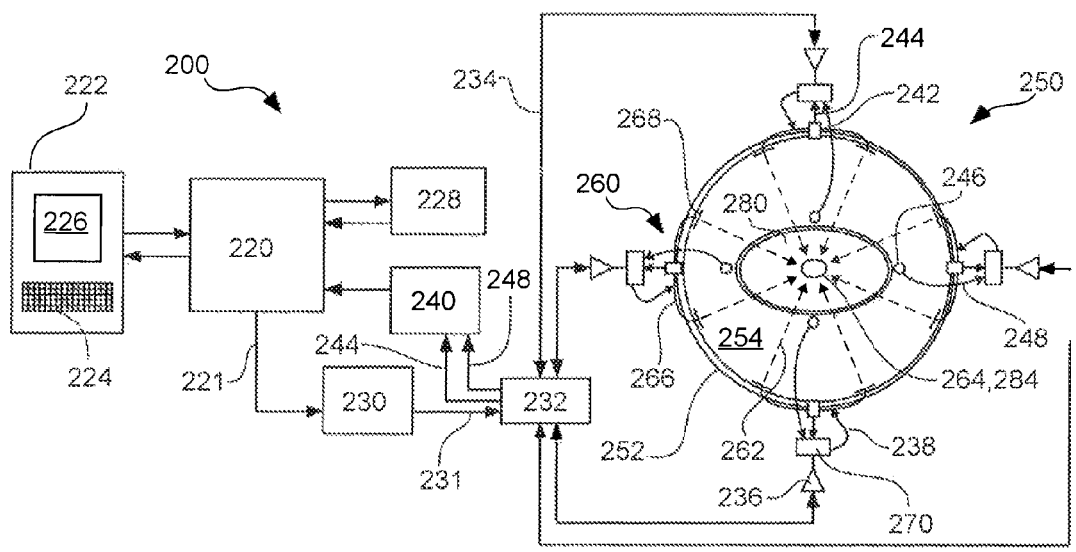
FIG. 12 is a schematic diagram of a hyperthermia treatment system and target body, in accordance with another representative embodiment.
Figure 13:
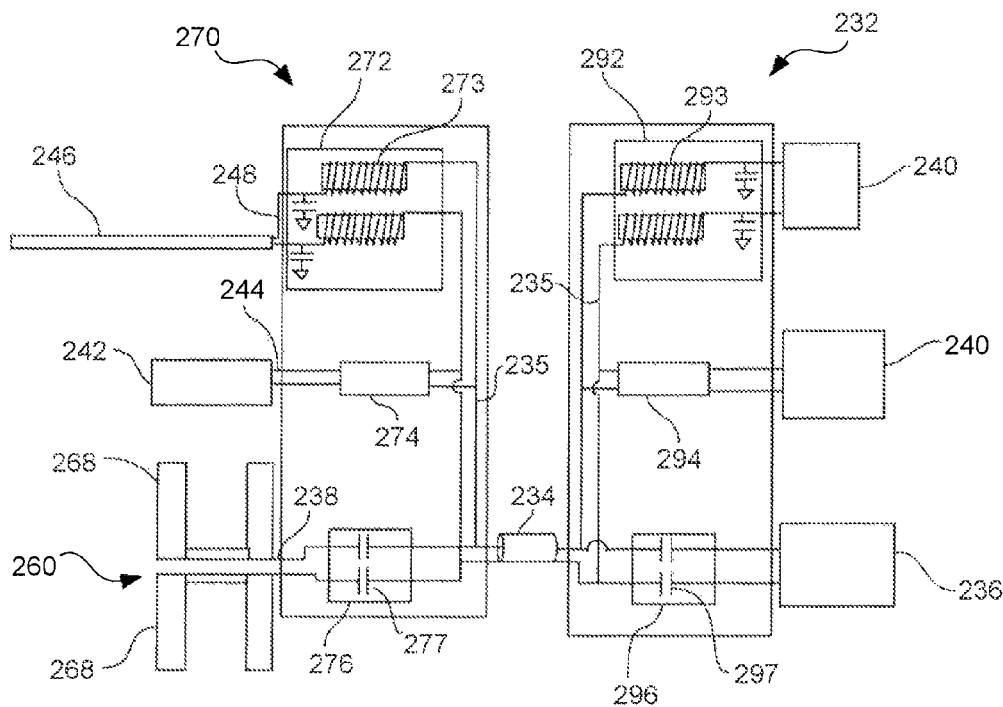
FIG. 13 is a wiring diagram of an electronic circuit for use with the hyperthermia treatment system FIG. 12.

Referring now to FIGS. 12-13, illustrated therein is another embodiment 200 of the hyperthermia treatment system in which the outputs 244 from the displacement measurement system 242 and/or the outputs 248 from the E-field measurement system 246 are multiplexed together into the EMR power signal channel 234 to reduce the number of cables entering the applicator array 250. Like the embodiments described above, the representative treatment system 200 can include a central processor unit 220 having an interactive feedback relationship with each of its elements, such as the control panel 222 having an input device 224 and a display 226, one or more memory devices 228, and one or more EMR power sources 230 which provide the EMR power to a surrounding array 250 of EMR applicators 260. As before, the EMR power source 230 can provide a primary EMR power signal 231 to a power splitter 232, either passive or active, that divides the power signal into a plurality of signal cables or channels 234, each carrying EMR power signals of substantially equal power and phase.

In contrast to the eight EMR signal channels described above, however, the power splitter 232 can divide the power signal into four signal cables 234, which can then be feed through an amplifier 236 and into four central energy supply connections 270 which feed four EMR applicators 260, such as the four dipole antenna pairs previously described and arrayed in FIGS. 2-3. From the central energy supply connections 270 the EMR power signal can then be directed through cables 238 to the joining sections 266 for the upper and lower radiating portions of the dipole-pair applicators. The joining sections 266 (which can be located outside the non-conductive housing or casing 252) can in turn carry the EMR power signal to the radiating arms 268 (which can be located inside and surrounded by the water inside the fluid-filled bolus 254) that are sized and tuned to radiate the EMR energy output 262 towards the center of the applicator array 250, where it is combined and concentrated with the other EMR radiation outputs 262 to form the focal region 264 located about the longitudinal center axis, and which is shown in FIG. 12 as being aligned with the selected region 284 of the target body 280 to be heated.

In one aspect the representative hyperthermia treatment system 200 can include a combined ultrasound distance and E-field sensor monitoring system having eight separate cable channels for monitoring both the position to the outer surface of the target body and the strength of the E-field on anterior, posterior, right, and left body surfaces. It is to be appreciated that the DC measurements from the E-field detectors 246 can be directed to an E-field sensor monitoring system directly with separate cabling or through a multiplexed configuration to enable the DC signal to utilize the same coaxial cables 234 used to carry the heating EMR power signal to the dipole arrays. Likewise, the ultrasound distance signals 244 could also be passed through independent cabling or multiplexed into these same EMR power signal transmission line channels 234.

A wiring diagram for a multiplexing central energy supply connector 270 and a de-multiplexing power splitter 232 connected together with an EMR power signal cable or channel 234, which can be a coaxial cable, is provided in FIG. 13. Within the central energy supply connector 270, the EMR power signal circuit 235 can be further divided into three circuits, one of which can carry the EMR power signal through a high pass filter 276 that filters out any low-frequency signal-components embedded in the power signal while allowing the high-frequency EMR power signal (which generally falls within the radio frequency (RF) and microwave frequency ranges on the electromagnetic spectrum) to pass directly through to the EMR applicator 260 via connector cables 238. In one aspect the high pass filter can utilize a capacitor 277 to filter out the low-frequency signal components.

As stated above, the hyperthermia treatment system 200 can include a displacement measurement system 242 (such as the ultrasound distance detector system described above) in combination with an E-field measurement system 246. The displacement measurement system 242 can be used to monitor the positional changes of the target body 280 relative to the applicator array 250, while the E-field measurement system 246 can be used to monitor the resulting heating pattern balance and shifting of the E-field that would be a result of these positional changes. The output 244 from the displacement measurement system 242, which can comprise an intermediate-frequency AC signal, can be directed into the central energy supply connector 270 where it passes through a band pass filter 274 before connecting with the EMF power signal circuit 235. Likewise, the output 248 from the displacement measurement system 246, which can comprise a DC signal, can also be directed into the same central energy supply connector 270 where it passes through a DC pass filter 272 which includes a plurality of inductors 273 before it also is connected with the EMF power signal circuit 235. Thus, both the displacement measurement system outputs 244 and the E-field measurement outputs 248 can be carried back to the monitoring and control portion of the hyperthermia treatment system 200 using the same coaxial cables 234 that are used to direct the heating RF power to the EMR applicator or dipole antenna array 250.

To break out the displacement measurement system outputs 244 and the E-field measurement outputs 248 from the EMF power signal circuit 235, a de-multiplexing circuit arrangement can also be integrated in the power splitter 232. Specifically, the power splitter can include a high-pass filter 296 that prevents any extraneous DC or intermediate frequency signals from being passed to the EMR power source, and which in one aspect can comprise a capacitor 297 to filter out the lower-frequency components. The de-multiplexing power splitter 232 can also isolate the intermediate-frequency displacement measurement signal 244 from the EMF power signal circuit 235 with a band pass filter 294, which displacement measurement input then can be received into the monitoring unit 240. The power splitter 232 can further include a DC pass filter 292 comprising a plurality of inductors 293 for separating out the E-field measurement signal 248 from the EMF power signal circuit 235, which can also be receiving into the monitoring unit 240. Once received, the monitoring unit 240 can then convert the analog AC inputs 244 from displacement detectors 242 and the analog DC inputs 248 from the electric field detectors 246 into digitized data suitable for communication with the CPU via connection line 241, to record and monitor the position of the target body and the progress of the treatment cycle, etc.

A schematic diagram of a target body 340 supported within an array 310 of electromagnetic radiation applicators 322, 323 is illustrated in FIGS. 14 and 15A-15C, in accordance with yet another representative embodiment 300. Although not drawn therein, it is to be recognized that target body is supported within the bolus 330 with the support mechanism described above, and that both the support mechanism and the target body can be moved together within the applicator array 310 by the positioning mechanism, also as described above.

Figure 14:
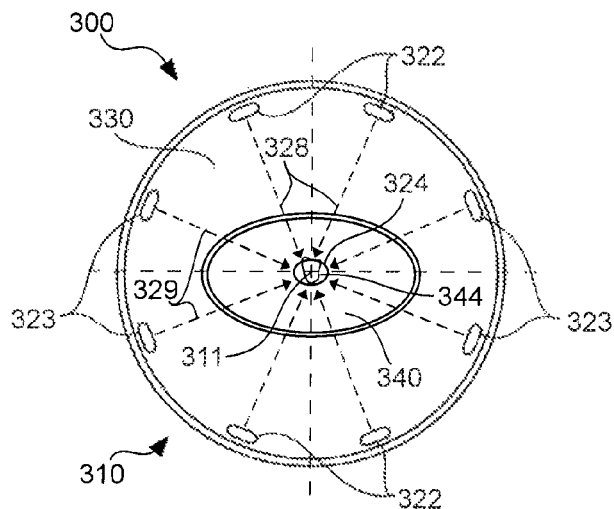
FIG. 14 is a schematic diagram of a target body supported within an array of electromagnetic radiation applicators, in accordance with another representative embodiment.

Referring first to FIG. 14, it can be seen that the target body 340 may be centered within the array and that selected region 344 to be heated may be aligned with the focal region 324 created by the converging outputs 328, 329 from the plurality of EMR applicators 320. It can also be noted that while the distances that each of the radiation outputs 328, 329 must travel to reach the longitudinal center axis 311 of the array 310 are substantially the same, the radiation outputs 328 emitted from the four more vertically-orientated EMR applicators 322 travel more distance through the water-filled bolus 330 and less distance through the target body 340 than do the radiation outputs 329 emitted from the four more horizontally-orientated EMR applicators 323, which by reason of the elliptical shape of the target body travel less distance through the water-filled bolus 330 and more distance through the target body 340. The wavelength in the water and the tissue is quite similar, but typically the body wavelength is about 10% larger than that of the water. This difference however, is not significant in resulting in a defocusing of the energy.

Based on the discussion above regarding the interaction between the E-fields emitted by the plurality of EMR applicators 320, a substantially transparent medium such as the fluid-filled bolus 330 and an attenuating or lossy medium such as the target body 340, it is to be appreciated that the vertically-orientated EMR outputs 328 can be more effective in penetrating to the focal region 324 than the horizontally-orientated EMR output 329. Nevertheless, since the target body 340 can be centered within the applicator array 310 in FIG. 14, the focal region 324 can remain substantially centered around the longitudinal center axis 311 of the applicator array 310.

In cases where the selected region 344 of the target body 340 to be heated is not located in the center of the target body, the positioning mechanism described above can be used to move target body 340 so that the selected region 344 aligns with the longitudinal center axis 311 of the applicator array 310 and with the focal region 324. However, one may appreciate that the interaction between the target body's attenuating medium and the various EMR outputs 328, 329 from the EMR applicators 322, 323 can cause the focal region 324 to shift away from the longitudinal center axis 311 of the applicator array 310. This can be numerically modeled and predicted as well as characterized or measured by body equivalent phantom testing.

Figure 15A:
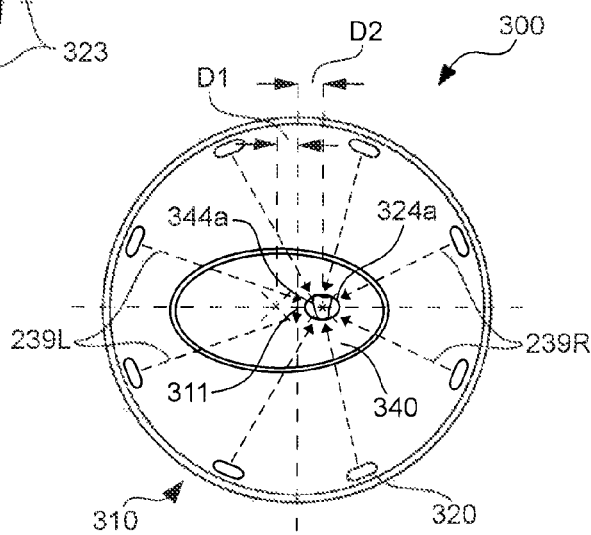
FIGS. 15A-15C together illustrate the effects of displacing the target body within the array of electromagnetic radiation applicators, in accordance the embodiment of FIG. 14.

For example, as shown in FIG. 15A, the selected region 344a of the target body 340 to be heated can be located to the right of the target body's center, so that the positioning mechanism can be activated to move the target body to the left and bring the selected region 344a into alignment with the longitudinal center axis 311 of the applicator array 310, and with the focal region 324a. However, moving the target body 340 to the left by distance D1 can increase the distance that the radiation outputs 329L emitted from left-most EMR applicators must travel through the lossy target body by distance D1, in relation to the correspondingly reduced distance by that radiation outputs 329R emitted from right-most EMR applicators must travel through the lossy target body. As a result, the focal region 324a can shift to the right, or opposite the displacement of the target body, and away from the longitudinal center axis 311 of the applicator array 310 by a distance D2. Accordingly, the hyperthermia treatment system 300 can be adapted to compensate for lateral displacement or shifting of the focal region 324a in response to the interaction between the combined radiation outputs and the target body 340 by reducing the amount of lateral displacement of the target body until the selected region 344a to be heated and the focal region 324a are brought into alignment.

Figure 15B:
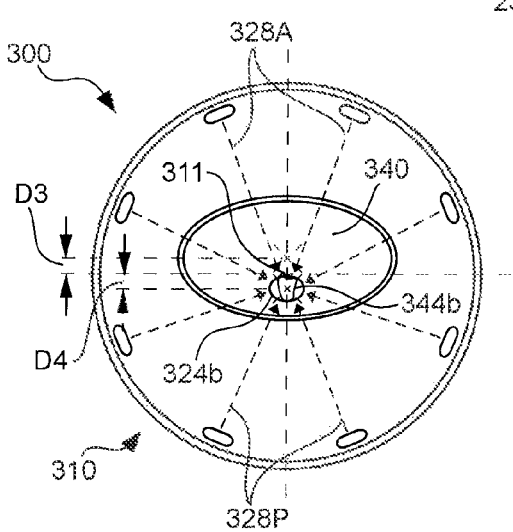

Similarly, as shown in FIG. 15B, the selected region 344b of the target body 340 to be heated can be located below the target body's center, so that the positioning mechanism can be activated to move the target body upwards and bring the selected region 344b into alignment with the longitudinal center axis 311 of the applicator array 310. However, moving the target body 340 upwards by distance D3 can increase the distance that the radiation outputs 328A emitted from anterior-most EMR applicators must travel through the lossy target body by D3, in relation to the reduced distance by that radiation outputs 328P emitted from posterior-most EMR applicators must travel through the lossy target body. As a result, the focal region 324b can shift downward or opposite the displacement of the target body, and away from the longitudinal center axis 311 of the applicator array 310 by a distance D4. Accordingly, the hyperthermia treatment system 300 also can be adapted to compensate for vertical displacement of the focal region 324b in a vertical direction in response to the interaction between the combined radiation outputs and the target body 340 by reducing the amount of vertical displacement of the target body, until the selected region 344b to be heated and the focal region 324b are brought into alignment.

Figure 15C:
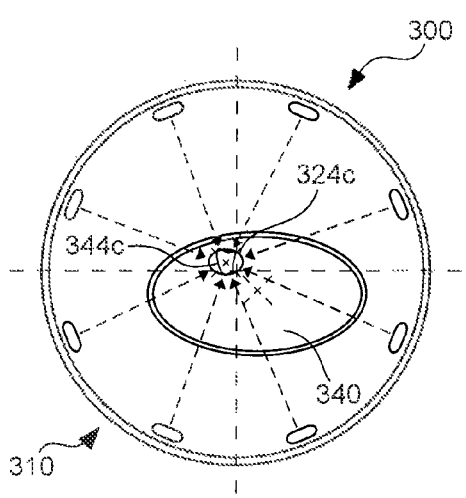

As can be appreciated by one of skill in the art, the hyperthermia treatment system 300 also can be adapted to compensate for a mixed lateral and vertical displacement of the focal region 224c in response to the interaction between the combined radiation outputs and the target body 240 by reducing the amount of lateral and vertical displacement provided to the target body by the positioning mechanism, until the selected region 244c to be heated and the focal region 324c are brought into alignment, as shown in FIG. 15C.

Compensation for the displacement of the focal region away from the longitudinal center axis of the applicator array due to the interaction of the emitted fields and the body created by the displaced target body can be accomplished in a variety of ways. For instance, with reference to FIG. 1, in one aspect the interaction affects can be measured and tabulated using trial target bodies 80 having dielectric characteristics that are identical or substantially similar to those of a living patient, and which measurements can be programmed into a computer program that is uploaded and stored in the computer-readable memory 28 for access by the control system's CPU 20 to predict the location of the focal region 64 with respect to the selected region 84 to be heated.

In another aspect the radiated field interactive affects can be calculated using numerical processing and methods such as finite element analysis, etc., the results of which can also be tabulated and programmed into a computer program that is subsequently installed onto in the computer-readable memory 28 and accessed by the control system's CPU module 20 and applied to predict the location of the focal region 64 with respect to the selection region 84 to be heated. In yet another aspect, moreover, the control system's CPU 20 can be programmed to accept inputs 48 from an E-field measurement system 46 which, in combination with inputs 44 from a positional measurement system 42, can be used to calculate the anticipated location of the shifted focal region 64 after repositioning of the target body by the positioning mechanism described and illustrated with reference to FIGS. 4-7. It is to be appreciated that combinations of these various methods and programs are also recognized and contemplated, and are considered to fall within the scope of the present invention.

Figure 16:
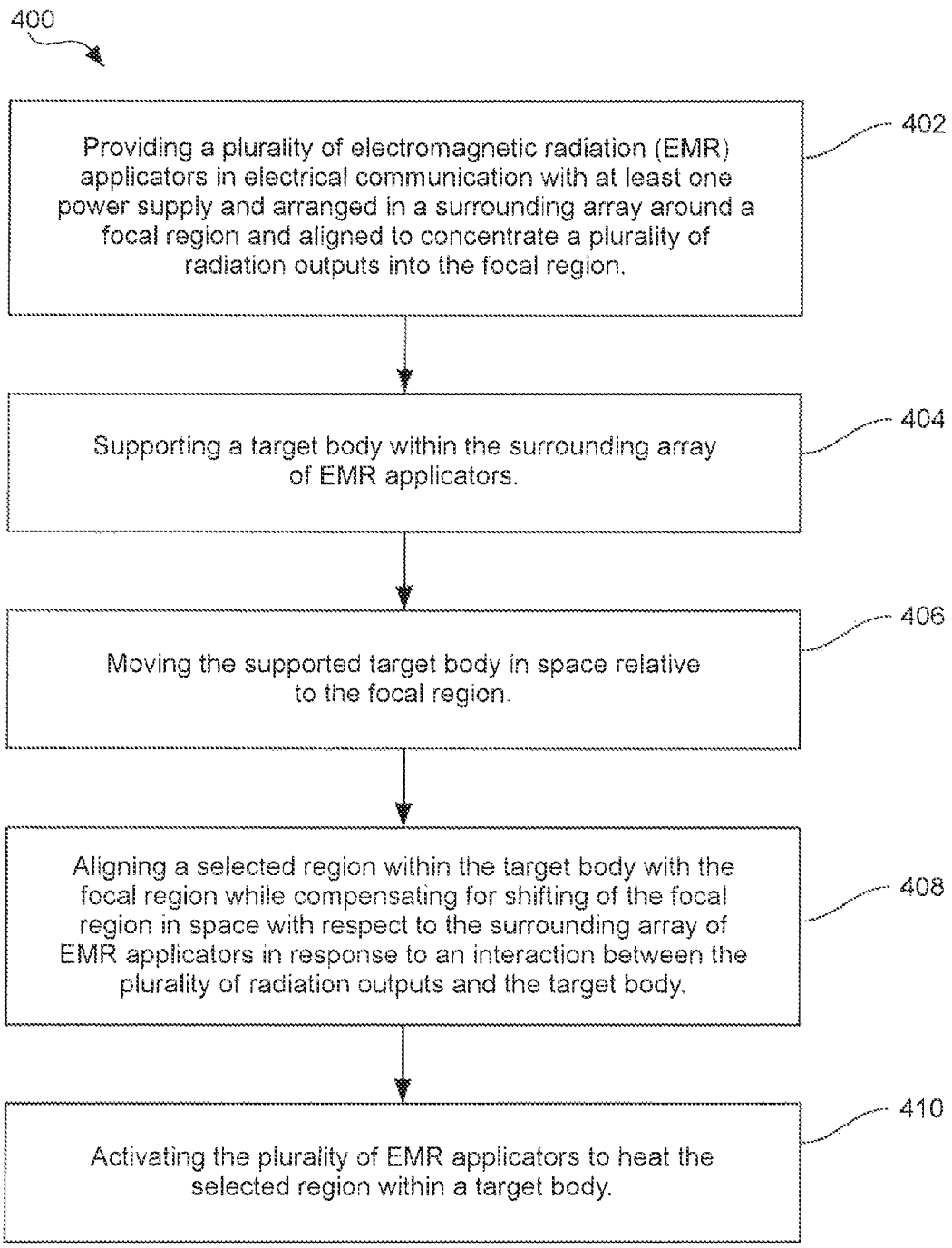
FIG. 16 is a flowchart depicting a method of heating a selected region within a target body, in accordance with yet another representative embodiment.

FIG. 16 is a flowchart that depicts a method 400 of heating a selected region within a target body, in accordance with yet another representative embodiment. The method 400 includes the step of providing 402 a plurality of electromagnetic radiation (EMR) applicators in electrical communication with at least one electromagnetic radiation power source and arranged in a surrounding array around a focal region to concentrate a plurality of radiation outputs into the focal region, and wherein a power and phase of each radiation output is substantially constant. The method 400 also includes the steps of supporting 404 a target body within the surrounding array of applicators, moving 406 the supported target body in space relative to the focal region, and aligning 408 the selected region within the target body with the focal region while compensating for a shifting of the focal region in space with respect to the surrounding array of EMR applicators in response to an interaction between the plurality of radiation outputs and the target body. The method 400 further includes the step of activating 410 the plurality of EMR applicators to heat the selected region within a target body.

In another aspect, the method 400 can also include the step of filling a flexible bolus between the surrounding array of applicators and the supported target body with a high-dielectric fluid that conveys the radiation output between the applicators and the target body. The filling of the flexible bolus can take place either before or after the target body has been moved so that the selected region within the target body is aligned with the focal region, and prior to the activation of the plurality of electromagnetic applicators.

The foregoing detailed description describes the invention with reference to specific representative embodiments. However, it will be appreciated that various modifications and changes can be made without departing from the scope of the present invention as set forth in the appended claims. The detailed description and accompanying drawings are to be regarded as illustrative, rather than restrictive, and any such modifications or changes are intended to fall within the scope of the present invention as described and set forth herein.

More specifically, while illustrative representative embodiments of the invention have been described herein, the present invention is not limited to these embodiments, but includes any and all embodiments having modifications, omissions, combinations (e.g., of aspects across various embodiments), adaptations and/or alterations as would be appreciated by those skilled in the art based on the foregoing detailed description. The limitations in the claims are to be interpreted broadly based on the language employed in the claims and not limited to examples described in the foregoing detailed description or during the prosecution of the application, which examples are to be construed as non-exclusive. For example, any steps recited in any method or process claims, furthermore, may be executed in any order and are not limited to the order presented in the claims. The term "preferably" is also non-exclusive where it is intended to mean "preferably, but not limited to." Accordingly, the scope of the invention should be determined solely by the appended claims and their legal equivalents, rather than by the descriptions and examples given above.

What is claimed and desired to be secured by Letters Patent is:

1. A hyperthermia treatment system for heating a selected region within a target body, comprising:
    at least one electromagnetic radiation power source;
    a plurality of electromagnetic radiation applicators in electrical communication with the at least one power source and arranged in a surrounding array around a focal region to concentrate a combined radiation output into the focal region;
    a support mechanism adapted to support the target body within the surrounding array of applicators;
    a positioning mechanism adapted to move the support mechanism and align the selected region within the target body with the focal region, and
    a displacement measurement system adapted to collect at least one positional measurement of the target body relative to the surrounding array of applicators.

2. The treatment system of claim 1, wherein the positioning mechanism is adapted to compensate for movement of the focal region in response to an interaction between the combined radiation output and the target body.

3. The treatment system of claim 1, wherein both a phase output and a power output of each of the plurality of applicators is substantially constant.

4. The treatment system of claim 1, wherein the at least one power source is a power source common to the plurality of applicators.

5. The treatment system of claim 4, wherein a power output of the common power source is substantially-equally divided among the plurality of applicators.

6. The treatment system of claim 1, wherein the surrounding array of applicators has a longitudinal center axis and the positioning mechanism is adapted to move the support mechanism and supported target body in at least one plane orientated perpendicular to the longitudinal center axis.

7. The treatment system of claim 1, wherein the displacement measurement system is selected from the group consisting of a mechanical scale, an electronic scale, a rotatable mechanical ruler, a dielectric contact bar, an ultrasonic position detector, an optical position detector, a laser position detector, and combinations thereof.

8. The treatment system of claim 1, wherein the at least one positional measurement is selected from the group consisting of a direct mechanical measurement, an ultrasonic distance measurement, a light distance measurement, and combinations thereof.

9. The treatment system of claim 1, wherein the at least one positional measurement comprises at least one of a top, bottom and opposite side perimeter locations of the target body.

10. The treatment system of claim 1, wherein an output signal channel from the displacement measurement system is combined with a power signal channel from the at least one power source.

11. The treatment system of claim 1, comprising a radiated energy measurement device configured to collect at least one applied radiated energy measurement of the target body relative to the surrounding array of applicators.

12. The treatment system of claim 11, wherein the applied radiated energy measurement device comprises an E-field detector.

13. The treatment system of claim 11, wherein the at least one applied radiated energy measurement comprises at least one of a top, bottom and opposite side perimeter locations of the target body.

14. A hyperthermia treatment system for heating a selected region within a target body, comprising:

at least one electromagnetic radiation power source;

a plurality of electromagnetic radiation applicators in electrical communication with the at least one power source and arranged in a surrounding array around a focal region to concentrate a combined radiation output into the focal region;

a support mechanism adapted to support the target body within the surrounding array of applicators;

a positioning mechanism adapted to move the support mechanism and align the selected region within the target body with the focal region; and a radiated energy measurement device configured to collect at least one applied radiated energy measurement of the target body relative to the surrounding array of applicators;

wherein an output signal channel from the radiated energy measurement device is combined with a power signal channel from the at least one power source.

15. A hyperthermia treatment system for heating a selected region within a target body, comprising:

at least one electromagnetic radiation power source;

a plurality of electromagnetic radiation applicators in electrical communication with the at least one power source and arranged in a surrounding array around a focal region to concentrate a combined radiation output into the focal region;

a support mechanism adapted to support the target body within the surrounding array of applicators; and a positioning mechanism adapted to move the support mechanism and align the selected region within the target body with the focal region;

wherein a driver device actuating the positioning mechanism is selected from the group consisting of a hydraulic drive, a pneumatic drive, an electric-motor drive and a mechanical gear drive, and combinations thereof.

16. The treatment system of claim 1, further comprising a flexible bolus filled with a high-dielectric fluid between the surrounding array of applicators and the supported target body that conveys the radiation output between the applicators and the target body.

17. A non-invasive hyperthermia system for heating a treatment region within a target body, comprising:

a power source;

a plurality of electromagnetic radiation applicators in electrical communication with the power source and arranged in a surrounding array around a focal region and aligned to concentrate a plurality of radiation outputs of substantially constant power and phase into the focal region;

a support mechanism adapted to support a target body within the surrounding array of applicators; and a positioning mechanism adapted to move the support mechanism and supported target body in at least one plane orientated perpendicular to a longitudinal center axis of the surrounding array and to align the treatment region with the focal region, wherein the positioning mechanism is adapted to compensate for shifting of the focal region away from the longitudinal center axis in response to an interaction between the plurality of radiation outputs and the target body.

18. A method of heating a selected region within a target body, comprising:

providing a plurality of electromagnetic radiation applicators in electrical communication with at least one power source and arranged in a surrounding array around a focal region to concentrate the plurality of radiation outputs into the focal region, and wherein a power and phase of each radiation output is substantially constant;

supporting a target body within the surrounding array of applicators;

moving the supported target body in space relative to the focal region;

aligning the selected region within the target body with the focal region while compensating for a shifting of the focal region in space in response to an interaction between the plurality of radiation outputs and the target body; and activating the plurality of electromagnetic applicators to heat the selected region within a target body.

19. The method of claim 18, further comprising filling a flexible bolus between the surrounding array of applicators and the supported target body with a high-dielectric fluid that conveys the radiation output between the applicators and the target body.

20. The method of claim 18, further comprising monitoring at least one positional measurement at a perimeter location of the target body relative to the surrounding array of applicators.

21. The method of claim 20, further comprising monitoring at least one applied radiated energy measurement at a perimeter location of the target body relative to the surrounding array of applicators.

22. The method of claim 21, further comprising combining the at least one positional measurement with the at least one applied radiated energy measurement to determine an inferred applied radiated energy measurement at the selected region within a target body.

\* \* \* \* \*